(12) United States Patent
Reneker et al.

(10) Patent No.: US 9,023,376 B2
(45) Date of Patent: May 5, 2015

(54) NANOFIBER-REINFORCED COMPOSITION FOR APPLICATION TO SURGICAL WOUNDS

(75) Inventors: Darrell H. Reneker, Akron, OH (US); Sureeporn Tripatanasuwan, Bangkok (TW); Daniel J. Smith, Stow, OH (US)

(73) Assignee: The University of Akron, Akron, OH (US)

( * ) Notice: Subject to any disclaimer, the term of this patent is extended or adjusted under 35 U.S.C. 154(b) by 863 days.

(21) Appl. No.: 12/492,507

(22) Filed: Jun. 26, 2009

(65) Prior Publication Data

US 2009/0324680 A1 Dec. 31, 2009

Related U.S. Application Data

(60) Provisional application No. 61/076,387, filed on Jun. 27, 2008.

(51) Int. Cl.
| | | |
|---|---|---|
| *A61L 26/00* | (2006.01) | |
| *A61L 31/12* | (2006.01) | |
| *A61L 31/04* | (2006.01) | |
| *D01D 5/00* | (2006.01) | |
| *A61B 19/00* | (2006.01) | |
| *A61F 2/00* | (2006.01) | |

(52) U.S. Cl.
CPC ....... *A61L 31/127* (2013.01); *A61B 2019/4884* (2013.01); *A61F 2/0063* (2013.01); *A61F 2002/009* (2013.01); *A61L 31/042* (2013.01); *A61L 2400/12* (2013.01); *D01D 5/0076* (2013.01)

(58) Field of Classification Search
USPC ........................................................ 424/423
See application file for complete search history.

(56) References Cited

U.S. PATENT DOCUMENTS

| | | | |
|---|---|---|---|
| 5,395,383 A * | 3/1995 | Adams et al. ................. | 606/151 |
| 6,382,526 B1 | 5/2002 | Reneker et al. | |
| 6,520,425 B1 | 2/2003 | Reneker | |
| 6,695,992 B2 | 2/2004 | Reneker | |
| 6,821,479 B1 | 11/2004 | Smith et al. | |
| 2003/0017208 A1 | 1/2003 | Ignatious et al. | |
| 2006/0148978 A1 | 7/2006 | Reneker et al. | |
| 2006/0204738 A1 * | 9/2006 | Dubrow et al. ............ | 428/292.1 |

(Continued)

FOREIGN PATENT DOCUMENTS

| | | |
|---|---|---|
| EP | 0 543 499 A1 | 5/1993 |
| WO | WO 2005/079335 A2 | 9/2005 |

(Continued)

OTHER PUBLICATIONS

Grafe, et al. Nanofiber Webs from Electrospinning, *5th Intl. Conference at Nonwovens in Filtration*, Stuttgart Germany, Mar. 2003.
Han, et al., Buckling of Jets in Electrospinning, *Polymer*, vol. 48, Issue 20, pp. 6064-6076 (2007).
Zufan, Electrospinning of Nanofibers, *Laboratory for Droplet and Particle Technology*, University of Illinois at Chicago, Aug. 4, 2005.

*Primary Examiner* — Michael B. Pallay
(74) *Attorney, Agent, or Firm* — Renner Kenner Greive Bobak Taylor & Weber

(57) ABSTRACT

A nanofiber-reinforced composition suited to applying to a wound site in a human body includes a carrier liquid and nanofibers dispersed therein in the carrier liquid. The viscosity of the composition is such that it is able to be applied through a tube yet adhere proximate the wound site to provide a barrier layer which assists in healing of the wound by spacing it from neighboring organs.

30 Claims, 5 Drawing Sheets

(56) References Cited

U.S. PATENT DOCUMENTS

| | | |
|---|---|---|
| 2007/0207179 A1 | 9/2007 | Andersen et al. |
| 2008/0021545 A1 | 1/2008 | Reneker et al. |
| 2008/0027531 A1 | 1/2008 | Reneker et al. |
| 2008/0032934 A1 | 2/2008 | Ellis-Behnke et al. |
| 2008/0305139 A1* | 12/2008 | Sabetsky ........................ 424/422 |

FOREIGN PATENT DOCUMENTS

| | | | |
|---|---|---|---|
| WO | WO 2005/079339 A2 | 9/2005 | |
| WO | WO 2005079335 A2 * | 9/2005 | ................ A61F 2/06 |

* cited by examiner

NANOFIBER-REINFORCED COMPOSITION FOR APPLICATION TO SURGICAL WOUNDS

This application claims the priority benefit of U.S. Provisional Patent Application No. 61/076,387, filed Jun. 27, 2008, entitled: NANOFIBER-REINFORCED COMPOSITION FOR APPLICATION TO SURGICAL WOUNDS, the disclosure of which is incorporated herein by reference in its entirety.

BACKGROUND

The exemplary embodiment relates to a nanofiber-reinforced composition. It finds particular application in conjunction with the delivery of such a composition to a wound site within the body, and will be described with particular reference thereto. However, it is to be appreciated that the present exemplary embodiment is also amenable to other like applications.

Surgical procedures have been developed for performing pelvic surgery and other internal surgical operations with an operating laparoscope. The laparoscope is inserted into a trocar tube extending through an incision in the body into the pelvic area. The laparoscope typically includes an optical passage for viewing the surgical area and another passage for receiving the instruments that are used in performing surgery on the tissue inside the body. The laparoscope permits surgeries to be performed deep within the body without requiring a large incision and thus facilitates a more rapid healing.

At the surgical site, bands of fibrous scar tissue can cause adhesions to form. These adhesions can result in two normally separate organs being bound together. Thus, organs which would normally slide over each other tend to pull on each other, resisting healing. Adhesions can also cause pain by pulling on nerves. To reduce the formation of adhesions, techniques have been developed for applying an adhesion barrier to the surgical site. The adhesion barrier may be formed of fine fabric biodegradable material which separates the organ on which the operation was performed from neighboring tissue. One problem in applying such a barrier is that it is difficult to insert the fabric material through a small diameter tube. Thus, in some procedures, a trocar with sufficient diameter to carry the rolled up fabric barrier as well as grasping forceps for physically unrolling the fabric barrier and manipulating the fabric barrier into position is used. Alternatively, a larger incision may be made to allow access for forceps to the surgical site. Both of these procedures, to some degree, negate the advantages of laparoscopic surgery.

Nanofibers have found use in medical applications. U.S. Publication Nos. 2008/0021545 and 2008/0027531, both to Reneker, et al. disclose nanofibrous coatings on medical devices, such a surgical mesh or stent. The nanofibers are spun directly onto a substrate and may be mechanically attached later. However, such applications do not permit the nanofibers to be inserted through a tube, such as a laparoscope, to a wound site.

The exemplary embodiment provides a biocompatible nanofiber-reinforced composition suited to use as an adhesion barrier and method for applying the composition to a surgical site which overcomes the above-referenced problems, and others.

BRIEF DESCRIPTION

In accordance with one aspect of the exemplary embodiment, a nanofiber-reinforced composition includes a carrier liquid and nanofibers dispersed in the carrier liquid.

The nanofiber-reinforced composition of this aspect may have a viscosity which allows it to pass through a tube having a diameter of less than 1 cm while being sufficiently viscous for the composition to adhere to a wound site.

The nanofiber-reinforced composition may have a Brookfield viscosity of at least 5,000 cPs at a temperature of 25° C. and a rotation speed of 20 revolutions per minute.

The nanofiber-reinforced composition may have a viscosity of at least 10,000 cPs at a temperature of 25° C. and a rotation speed of 20 revolutions per minute.

The nanofiber-reinforced composition may have a viscosity of no more than 100,000 cPs at a temperature of 25° C. and a rotation speed of 20 revolutions per minute.

The nanofiber-reinforced composition may have a viscosity of from 10,000 to 80,000 cPs at a temperature of 25° C. and a rotation speed of 20 revolutions per minute.

The nanofibers may be present in the composition at a concentration of at least 0.1 percent by weight.

The nanofibers may be present in the nanofiber-reinforced composition at a concentration of at least 0.5 percent by weight.

The nanofibers may be present in the nanofiber-reinforced composition at a concentration of up to 5 percent by weight.

The nanofibers in the composition may have a diameter of less than 3000 nm.

The nanofibers in the composition may have a diameter of at least about 10 nanometers.

The nanofibers in the composition may have a diameter of up to about 500 nanometers.

The nanofiber-reinforced composition may further include microfibers dispersed in the carrier liquid.

The microfibers may be present in the nanofiber-reinforced composition at a concentration of at least 0.1 percent by weight.

The microfibers may be present in the nanofiber-reinforced composition at a concentration of up to 5% percent by weight.

The microfibers and nanofibers may be present in the nanofiber-reinforced composition at a total concentration of less than 5% percent by weight.

The microfibers may have a diameter of at least 5 micrometers.

The microfibers may be formed from a different material to the nanofibers.

The carrier liquid may include a soluble sugar.

The soluble sugar may include dextran.

The soluble sugar may be present in the carrier liquid at a concentration of at least 20 weight percent.

The soluble sugar may have a weight average molecular weight of at least 50,000.

The nanofiber-reinforced composition may include at least one therapeutic agent.

The nanofiber-reinforced composition may include at least one of microfibers, platelets, flakes, dissolved substances, particles, colloids, and micelles, optionally incorporating therapeutic agents.

In another aspect, a method includes introducing the nanofiber-reinforced composition as described in any of the aspects above into a body of a human subject.

The method may include introducing the nanofiber-reinforced composition into the subject's body though a tube.

The tube may include an outlet defined by a pair of surfaces and the surfaces may be moved relative to one another as the nanofiber-reinforced composition is released into the body from the outlet. The relative movement of the two opposed surfaces may cause the nanofibers to form a structure in which regions of low concentrations of nanofibers are surrounded by high concentration regions of nanofibers, with a twisted texture resembling a loose chicken wire structure.

In introducing the composition, pressure may be applied to the composition to squeeze it through the tube.

The method may further include positioning the tube adjacent a wound site within the subject's body and introducing the composition through the tube to the wound site.

The introduced composition may form a barrier adjacent a wound site for limiting adhesion of the wound site to neighboring tissue.

In another aspect, a method of forming the nanofiber-reinforced composition of any of the aspects described above includes forming nanofibers and combining the nanofibers with the carrier liquid.

The combining may include electrospinning the nanofibers directly into the carrier liquid.

Microfibers may be dispersed in the carrier liquid prior to the introduction of the nanofibers.

The nanofibers may be allowed to conglutinate or buckle into coils prior to combining them with the carrier liquid.

In another aspect, an applicator includes a container which holds an amount of the nanofiber-reinforced composition of any of the aspects described above and a tube, fluidly connected with the container, for introducing the composition into a body of a subject.

The applicator may be configured for applying pressure to the nanofiber-reinforced composition.

The container may include a syringe barrel and the applicator may further include a piston for applying the pressure.

The applicator may include a laparoscope.

In accordance with another aspect, a method of providing an adhesive barrier at a wound site includes introducing a nanofiber-reinforced composition to a subject's body through a tube having an outlet positioned adjacent the wound site, the nanofiber-reinforced composition having a viscosity which causes it to adhere to the wound site or neighboring tissue to form an adhesive barrier thereon.

In this aspect, the nanofiber-reinforced composition may include a carrier liquid and nanofibers dispersed in the carrier liquid.

The nanofiber-reinforced composition may further include microfibers.

The nanofiber-reinforced composition used in the method may have a viscosity in the range of 10,000-80,000 cPs at a temperature of 25° C. and a rotation speed of 20 revolutions per minute.

DETAILED DESCRIPTION

Figure 1:
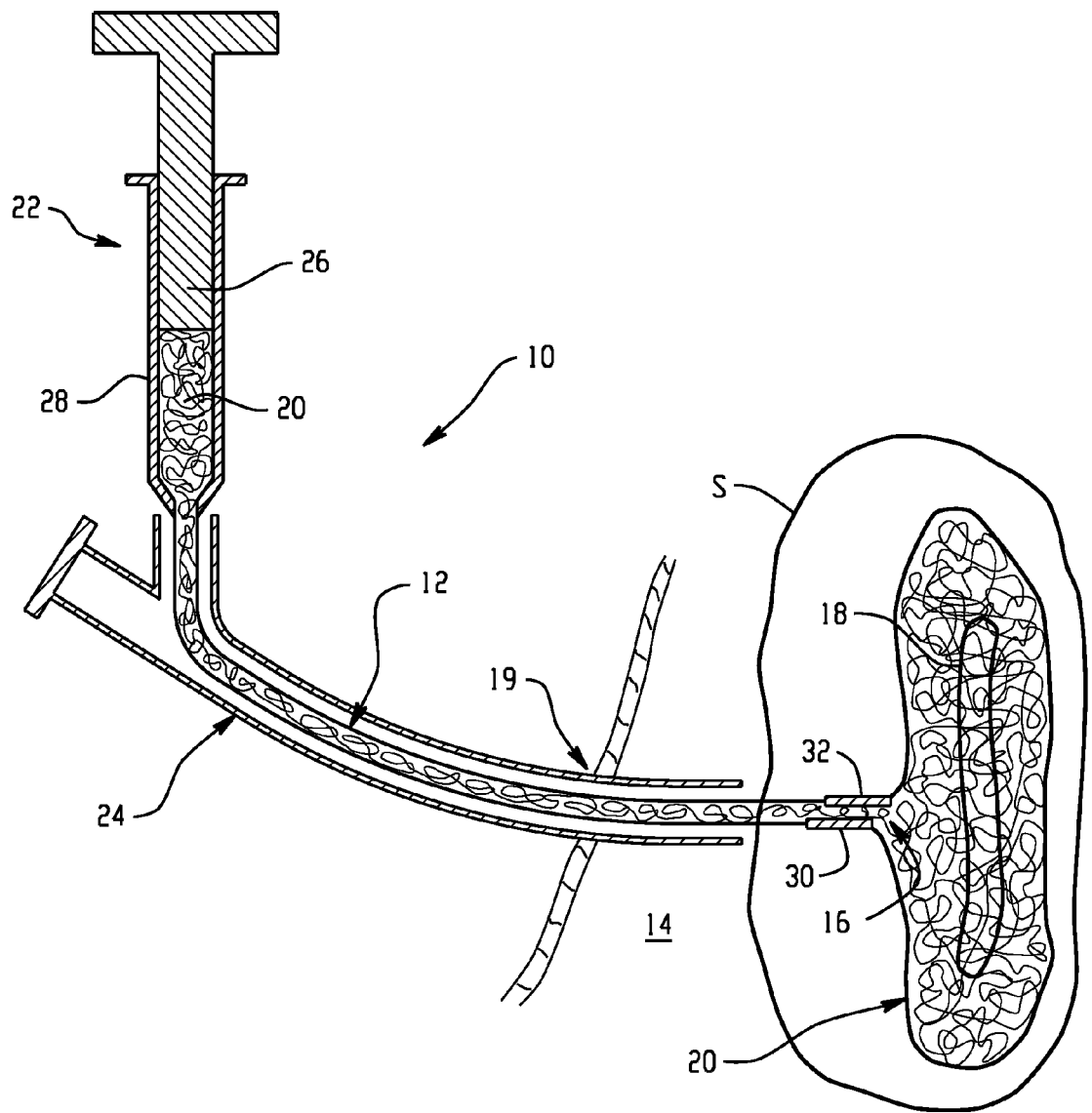
FIG. 1 is a schematic view of an applicator for administering a nanofiber-reinforced composition to a wound site.

In various aspects, a nanofiber-reinforced composition, applicator, and method of application of the nanofiber-reinforced composition to a surgical site are disclosed. The nanofiber-reinforced composition is formulated to have rheological properties, such as viscosity, which allow a mass of the composition to be delivered to a wound site, e.g., via a tube, such as a trocar tube or to be applied with forceps. The composition finds application in minimally invasive surgery, such as laparoscopic surgery, in which the nanofiber-reinforced composition is applied to the wound site to promote proper healing, for example, by reducing the possibility of healing attachment between the wound site and another part of the body. The exemplary composition can thus act as a barrier between the wound site and another organ or part of the same organ.

The exemplary reinforced composition is biocompatible. By "biocompatible," it is meant that the composition is compatible with a site within the human body to which it is applied without having toxic or injurious effects and/or is biodegradable. In general, the composition includes a mixture of biodegradable nanofibers dispersed in a biocompatible liquid.

In the following description, all percentages are expressed by weight, unless otherwise indicated.

The Nanofiber-Reinforced Composition

The nanofiber-reinforced composition is generally a viscous fluid material which includes nanofibers dispersed in a carrier liquid. The nanofiber-reinforced composition may further include one or more therapeutic agents, which may be incorporated into the fibers or separately dispersed in the carrier liquid. The composition may further include microfibers, platelets, flakes, dissolved substances, particles, colloids, and micelles, which in turn may incorporate therapeutic agents.

The nanofibers can form a loose network that reinforces the carrier liquid and allows it to be handled with forceps or tweezers, or injected through a tube. The nanofibers generally increase the viscosity of the carrier liquid. The rheological properties and other mechanical properties of the composition can be adjusted by varying one or more of nanofiber concentration, nanofiber length, molecular weight of a nanofiber forming polymer, and molecular weight of a sugar or other polymer in the carrier liquid.

Nanofibers are microscopic fibers having a length which is many times their diameter. In general, the nanofibers in the composition have a mean diameter ranging from about 3-3000 nanometers (nm). In one embodiment, the nanofibers may have a mean diameter of at least 10 nm and may have a mean diameter up to about 100 nm. The nanofibers may have a mean length which is at least ten times the mean diameter and can be at least 100 times the mean diameter. The mean length of the nanofibers may from about 100 nm to greater than one meter, e.g., from 1 mm-2 meters in length.

The nanofibers may be formed from virtually any suitable material that is capable of forming nanofibers and further that is biocompatible or which can be rendered biocompatible in the nanofiber-reinforced composition. Suitable materials for forming the nanofibers are generally polymeric materials, such as soluble or insoluble polymers. Examples of insoluble or sparingly soluble nanofiber-forming polymers which may be used for forming the nanofibers include poly(caprolactone), polyethylene terephthalate, fibrinogen, polyolefins, e.g., polyethylene and polypropylene, polyethylenimines, cellulose acetate and other optionally grafted cellulosics, poly(L-lactic acid), poly(ethyleneoxide), poly(hydroxyethylmethacrylate), poly(glycolic acid) and polyvinylpyrrolidone, polyethylene glycol, polyethylene oxazoline, polyesters, polyacrylic acid, polyacrylic acid esters, polyphosphezines, polycyanoacrylate, polyvinyl amines, polyethylene amines, polyacrylamides, cellulose, cellulose derivatives, proteins, polyorthoesters, polyanhydrides, polyketals, polyacetals, polyureas, polycarbonate, and combinations thereof.

Examples of soluble polymers include biodegradable polymers, such as proteins. Combinations of materials may be employed.

The nanofiber forming polymer may have a weight average molecular weight $M_w$ of at least about 5000 and in one embodiment, at least 30,000. The $M_w$ may be up to about 100,000, e.g., about 50,000-70,000.

The nanofibers may be present in the composition at a concentration of about 0.1-10% by weight. In one embodiment, the nanofibers are present at a concentration of at least 0.3% or at least about 0.5% by weight of the composition. In another embodiment, the nanofibers are present at up to about 5% by weight. In specific examples, the nanofibers constitute no more than 3% by weight, e.g., about 2 wt. % or less, and in one embodiment, about 1.5 wt. %, or less of the composition.

The carrier liquid can be any biocompatible liquid that is capable of wetting the nanofibers. Exemplary carrier liquids include aqueous and non-aqueous liquids, such as oils, polymer solutions, solutions of soluble sugars, oil-in-water emulsions, water-in-oil emulsions, and dispersions. Aqueous solutions containing water-soluble sugars which may be employed as the carrier liquid include solutions of monosaccharides (e.g., glucose, fructose, galactose), disaccharides (e.g., sucrose, lactose, maltose), trisaccharides, polysaccharides, such as dextran, and combinations thereof. The molecular weight of the dissolved sugar or other polymer can be selected so as to provide the composition with desired rheological properties.

An exemplary soluble polymer is a polysaccharide, such as dextran. The soluble sugar may have a weight average molecular weight $M_w$ which renders it soluble in water, e.g., $M_w$ is less than 500,000, e.g., less than about 300,000. In one embodiment, $M_w$ may be at least 10,000, e.g., at least 50,000, and in one specific embodiment, the sugar comprises dextran with a $M_w$ of 100,000-200,000. In another embodiment, the sugar has a molecular weight of about 500 or less, e.g., sucrose.

The concentration of the water soluble sugar in the carrier liquid (and/or composition) may be from about 1 wt. % to about 99 wt. % (or up to its maximum solubility in water). In one embodiment, the sugar is present in the carrier liquid/composition at a concentration of at least 20 wt. %, and in one embodiment, the sugar concentration in the carrier liquid/composition is less than 40 wt. %. For example, the sugar may be dextran at about 30 wt. %.

Exemplary combinations of nanofibers and carrier liquids include polycaprolactone in sugar (sucrose) syrup, and polycaprolactone in dextran solution.

The nanofiber-reinforced composition may additionally include microfibers. Microfibers are fibers which are substantially larger than the nanofibers and may have a mean diameter of from about 5 to 50 micrometers (μm). The microfibers may have a mean length from 1 mm to 500 mm. Exemplary microfibers include staple fibers, loosely twisted yarns, open networks, and woven or non-woven reinforcements. The microfibers may be biodegradable or biocompatible fibers. The microfibers may be present in the composition at a concentration of 0-10% by weight. In one embodiment, the concentration of the microfibers is at least 0.1 wt. %. In another embodiment, the concentration of the microfibers in the composition is no more than about 5 wt. %, e.g., about 3 wt. %, or less and in one embodiment, less than 1 wt. %.

The microfibers may be made from biodegradable or biocompatible materials for anti-adhesion applications. Microfibers can be made from other polymers for other applications. Exemplary polymers for forming microfibers include those described above for the nanofibers. In one embodiment, the microfibers are formed from a different material to the nanofibers.

Microfibers have several advantages in the exemplary compositions. In particular, microfibers can provide stiffness, provide greater separation between the surfaces of the organs, provide an additional means for stabilizing the network of nanofibers formed during application of the material and, because of their larger size than nanofibers, provide a longer time for healing before the fiber is degraded.

Where microfibers are included in the composition, the weight percent of nanofibers may be correspondingly reduced. In one embodiment, the total concentration of fibers (including microfibers and nanofibers) in the composition ranges from about 0.1-5% by weight, e.g., from 0.3-3 wt. %., and in one embodiment, 0.5-2 wt. %. The microfibers may range from 0-99 wt. % of the total fibers in the composition. In one embodiment, the ratio of nanofibers to microfibers in the composition by weight ranges from about 100:1 to 1:100, e.g., 20:1 to 1:20. In specific embodiments, the microfibers are present in the composition at no more than 50 wt. % of the total fibers, e.g., about 30 wt. % of the total fibers, or less, and in one embodiment, less than 10 wt. % of the total fibers.

In one embodiment, the nanofiber-reinforced composition includes flat platelets. The platelets may have a mean diameter of about 0.1 mm to 10 mm, e.g., about 0.2-2 mm, e.g., about 1 mm and a thickness which is less than half the diameter, e.g., about 0.5 mm, or less. They may be formed, for example, from a biodegradable polymer, such as poly(caprolactone), poly(L-lactic acid), poly(glycolic acid), poly(lactic-co-glycolic acid), poly(β-hydroxybuyrate), poly(acrylic acid), poly(hydroxylethylmethacrylate), protein, cellulose, cellulose derivatives, protein, polyanhydrides, and combinations thereof. The platelets may incorporate a therapeutic agent.

One reason for incorporation of platelets is that the shearing motion, during the spreading of the nanofiber-reinforced composition onto the surface of an organ, or during the sliding of one organ over an adjacent organ, can create rotational flow patterns that tend to twist the fibers together into yarn-like segments, with the axis of the yarn in a direction normal to the sliding direction. Sliding of the surfaces of the organs may also pull some of the fibrous material into long strands in the direction of the sliding motion. If too much of the fibrous material is twisted into yarn, the desired separation, that prevents adhesions of the organs, may not be maintained for a long enough time for healing. The addition of flat platelets of biodegradable polymer, with diameters of around a millimeter can reduce the rotational flow during sliding. The platelets should be thin enough to conform to the surface of the wound and thick enough and large enough to resist bending or scroll-like rolling during sliding of the adjacent organs or during the spreading of the material as it is applied to the surfaces of the organs.

Reinforcing fibers, in the form of conglutinated bending coils or patterns, may be created during the electrospinning process, by the attachment of fibers to each other at points of intersection. These may also be used to prevent the shearing flows in the reinforced fluid from concentrating the fibers into undesired yarns.

Bucking may be encouraged to form coils. Buckling coils are created when a wet jet impinges on a solid or liquid surface. The coiled nanofibers of 3 micron to 100 nanometer average diameters, e.g., with coil diameters of 3-100 microns, such as 5-50 nanometers, may improve the composition by increasing the interaction between the buckled fibers and the fluid. Additionally, desirable rheological properties may be achieved with reduced concentrations of nanofibers.

Therapeutic agents may be incorporated into the composition, e.g., within or attached to the nanofibers or otherwise dispersed in the carrier liquid. As used herein, a therapeutic agent can be any pharmaceutically acceptable agent, active substance, or drug having a therapeutic activity for use in a mammal, generally a human. The therapeutic activity may be prophylactic or for treatment of a medical condition or disease state. Exemplary therapeutic agents include, for example, analgesics, anti-inflammatory agents, anthelmintics, anti-arrhythmic agents, antibiotics, anticoagulants, antidepressants, antidiabetic agents, antiepileptics, antihistamines, antihypertensive agents, antimuscarinic agents, antimicrobacterial agents, antineoplastic agents, immunosuppressants, antithyroid agents, antiviral agents, anxiolytic sedatives (hypnotics and neuroleptics), astringents, beta-adrenoceptor blocking agents, blood products and substitutes, live cells, cardiac inotropic agents, corticosteroids, cough suppressants (expectorants and mucolytics), diagnostic agents, diuretics, dopaminergics (antiparkinsonian agents), haemostatics, immunological agents, lipid regulating agents, muscle relaxants, parasympathomimetics, parathyroid calcitonin and biphosphonates, prostaglandins, radiopharmaceuticals, sex hormones (including steroids), anti-allergic agents, stimulants and anorexics, sympathomimetics, thyroid agents, inhibitors, antipsychotics, vasodilators, and xanthines. Other materials may be incorporated into the carrier liquid or attached to the nanofibers. For example, proteins may be immobilized on the surface of nanofibers by conjugating activated carboxylic groups of the protein to the surface exposed amine groups of the nanofibers.

Examples of methods for incorporation of these agents into or onto nanofibers are disclosed, for example, in U.S. Publication Nos. 2006/0148978, 2008/0021545 and 2008/0027531, the disclosures of which are incorporated herein by reference in their entireties. In other embodiments, the therapeutic agents may be contained in microparticles, such as microspheres and/or microcapsules. Such microparticles are in particular useful in the treatment of cancer. The microparticles may be biodegradable and may be made from a biodegradable polymer such as a polysaccharide, a polyamino acid, a poly(phosphorester) biodegradable polymer, a polymers or copolymers of glycolic acid and lactic acid, a poly(dioxanone), a poly(trimethylene carbonate)copolymer, or a poly (α-caprolactone) homopolymer or copolymer. The microparticles may be in the form of microspheres that encapsulate the pharmaceutically active substance, such as the chemotherapeutic agent. The release of the therapeutic agent generally commences after the administration of the composition.

Other methods for sequestration and protection of proteins and other biological substances inside nanofibers, which may be used in the present nanofiber-reinforced composition are disclosed, for example, in U.S. Pat. No. 6,821,479, entitled PRESERVATION OF BIOLOGICAL MATERIALS USING FIBER-FORMING TECHNIQUES, to Smith, et al., the disclosure of which is incorporated herein by reference in its entirety. In some embodiments, reagents are separately contained in different nanofibers such that when an initiator is added, such as a solvent, the reagents react together to form a therapeutic agent. Such methods are disclosed, for example, in U.S. Pat. No. 6,737,447, entitled NITRIC OXIDE-MODIFIED LINEAR POLY(ETHYLENIMINE) FIBERS AND USES THEREOF, by Smith, et al., the disclosure of which is incorporated herein by reference in its entirety. Other techniques for incorporating therapeutic agents into nanofibers which may be used herein are disclosed, for example, in U.S. Pat. No. 7,235,295, entitled POLYMERIC NANOFIBERS FOR TISSUE ENGINEERING AND DRUG DELIVERY, by Laurencin, et al., and U.S. Pub. No. 2003/0017208 (WO2001054667A1), entitled ELECTROSPUN PHARMACEUTICAL COMPOSITIONS, by Ignatious, et al., the disclosures of which are incorporated herein by reference in their entireties.

Unique properties of the nanofiber-reinforced composition include its flow and mechanical properties. The nanofiber-reinforced composition has a viscosity which is sufficient to maintain the structural integrity of the composition as a mass. For example, a blob of the composition can be picked up on a spatula or with forceps. The viscosity is also suitable for rendering the composition sufficiently pliable to be inserted through a tube of an applicator extending through the body to a surgical site. The viscosity is also sufficient for the nanofiber-reinforced composition to adhesively adhere to the surgical site or neighboring tissue and serve as an adhesion barrier, without the need for any structural supporting substrate, such as a fabric, film, mesh, or the like. The adhesive barrier may maintain its structural integrity and so function as a barrier for hours or even one or more days within the body. During this time, the adhesive barrier may prevent contact of another organ or tissue with the wound site. The properties of the composition may allow it to flow over an organ to form the barrier.

As used herein, 'viscosity' refers to the Brookfield viscosity measured with a Brookfield HB viscometer fitted with a spindle number 6 at a temperature 25° C. The spindle rod diameter is 3.10 mm, the spindle disk diameter is 14.50 mm and the spindle disk thickness is 1.45 mm. The viscosity of the composition may be for example, at least about 5,000 cPs and can be up to about 100,000 cPs (1 cps=1 mPa s) at a rotation speed of 20 revolutions per minute. In one embodiment, the viscosity is from about 10,000-80,000 cPs under these conditions. In one specific embodiment, the viscosity is at least about 12,000 cPs or at least 20,000 cPs under these conditions. In another embodiment, the viscosity is less than about 70,000 cPs under these conditions.

Prior to addition of the nanofibers, the carrier liquid may have a viscosity of less than 10,000 cPs, e.g., 8000 cPs, or less, and in one embodiment, at least about 5000 cPs.

The exemplary composition can flow and can be stretched to a certain distance without breaking. Increasing the concentration of fibers in the carrier liquid tends to reduce its flowability, but increases mechanical strength. On the other hand, decreasing the concentration of fibers in viscous liquid tends to make it flow more easily with less resistance to extension. Accordingly, the composition can be tailored to particular applications by adjusting the concentrations of the components of the composition.

The elongation at break of the composition may be measured by drawing two tubes containing the material apart. The tubes used in the test may have an internal diameter of about 4 mm. The composition forms a thread between the two tubes as they are pulled apart, which eventually beaks. The distance between the tubes at break is measured. Compositions suitable as a barrier material generally elongate to at least 20 mm, e.g., 30 mm or more, and generally elongate less than about 60 mm before break. Compositions which elongate to about 10 mm or less at break are generally too runny to be suitable as a barrier material at a wound site. Compositions with an elongation of about 70 mm are generally too stiff to be easily applied laproscopically.

The Applicator and Application of the Composition to a Surgical Site

FIG. 1 illustrates an exemplary applicator 10 for applying the nanofiber-reinforced composition described above. The applicator includes a delivery tube 12, which is inserted into a person's body 14 and includes an outlet 16. The outlet can be positioned proximate a surgical site 18 within the body 14, here shown as a wound on surface S of an organ in the body. The tube is insertable in the body through an incision 19 in the skin or a natural body orifice. The tube 12 may be incorporated into a laparoscopic device, for example, by incorporation of one or more additional tubes (not shown) which run beside and/or concentric with the tube 12. The tube 12 may be of small diameter, as used in non-invasive surgery, e.g., laparoscopy. For example, the tube 12 may be less than 1 cm, e.g., 2-10 mm in diameter, e.g., 0.5 cm in diameter or less. An amount of the nanofiber-reinforced composition 20 is fed to the tube 12 from a container 22, which may be positioned outside the body 14. The exemplary container 22 is a syringe which feeds the composition 20 to the delivery tube 12 via a trocar 24.

The nanofiber-reinforced composition can thus be introduced directly to a living organism via a thin tube. For example, mechanical or manual pressure on a piston 26 of the syringe squeezes the composition out of a syringe barrel 28, from where it passes through the small diameter tube 12 and is released from the outlet onto to the wound site. Other methods of introducing the composition into a subject's body are also contemplated. For example the composition may be injected into the body with a hypodermic needle. In another embodiment, forceps or other tool are used to introduce a blob of the material to the body.

Using the exemplary applicator 10 or other applicator, the nanofiber-reinforced composition can be directly applied to a site 18, such as a target organ, bone, or other wound site. It can flow, spread and adhesively attach to the target organ. It can immediately act as a barrier to infection or rubbing without the need for further chemical reaction. It is therefore particularly suited to laparoscopic surgery. The composition can remain adhesively attached to the wound site for more than a day and up to several days, allowing the wound to heal.

Figure 5:
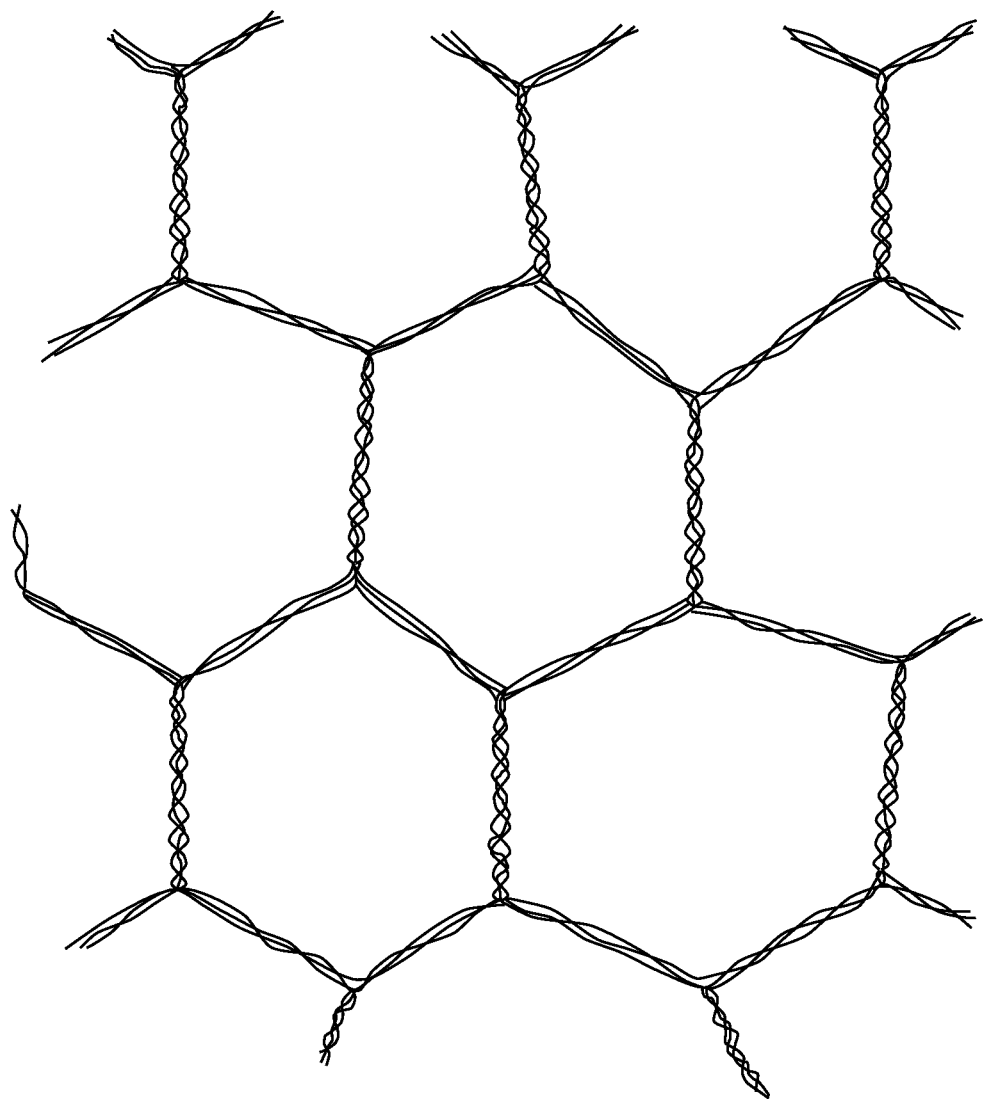
FIG. 5 illustrates an exemplary mesh-like structure formed from the nanofibers.

The outlet 16 of the tube may be shaped to create different patterns within the nanofiber-reinforced composition. Strategies for shearing the fiber-reinforced fluid as it is applied into deliberately caused patterns can create short, yarn-like segments that are distributed over the surfaces to be protected, and provide centimeter scale patterns that keep the fibers and yarn segments distributed over the surfaces, while avoiding winding an excessive fraction of the fibers into yarns. Deliberate shearing patterns may be created at the outlet 16 of the tube. For example, the outlet is in the form of plates 30, 32 which define substantially flat opposed surfaces between which the composition passes as it is released from the tube 12. The plates 30, 32 are moved relative to each other in a sliding pattern, for example, using a micromotor attached to one or both plates (not shown). This motion and/or motion of the outlet relative to the surface of the organ, creates a two dimensional wavelike pattern of the yarn-like segments. As a result, the undesired twisting of the reinforcing fibers after application is resisted by the larger scale network created during the application and spreading of the fiber reinforced fluid. The relative motion of the plates 30, 32 can create a polygonal network of partly twisted yarn fibers and partly stretched yarn in the composition with the appearance of chicken wire (FIG. 5) or an undulating wave pattern similar to hair styled with a Marcel wave. For example, a chicken wire appearance can be created by an outlet which includes opposed plates 30, 32, each having an array of flexible protrusions on the opposed surfaces. One or both of the plates can be moved relative to the other in approximately circular or other periodic motion. This movement of the protrusions creates regions of concentration of the fibers (the "chicken wire") which surround regions were the fibers are absent or more disperse. The creation of yarn-like networks and the increased separation of the organs due to the increased thickness of the yarn are both desirable for such applications. However, the formation of very large diameter yarns that concentrate most of the nanofibers/microfibers in the yarn, leaving other areas in which the wound could come into adhesion forming contacts with adjacent organs is to be avoided. Formation of networks of yarn-like segments appears to serve both these purposes.

Upon implantation, the nanofiber-reinforced composition 20 forms a barrier layer 30 on the surgical site. Over time, such as a few days, the carrier liquid component of the barrier disperses into the subject's blood or other body fluid and the nanofibers either degrade or pass into the body fluid along with the carrier fluid. A fluorescent dye or other label may be added to the composition to serve as a tracer which allows the location of the mass of composition to be determined during and after its implantation.

The nanofiber-reinforced composition 20 is particularly suited to use in a laparoscopic device, for example, for coating ovaries which have undergone laparoscopic surgery, to reduce contact with neighboring tissue.

Another application is in repair of hernias. For example, the composition may be flowed through small holes in a mesh, such as a mesh formed of polypropylene. The nanofibers may be used to improve the mechanical connection between the mesh and the herniated muscular structure. Techniques for applying the mesh are disclosed, for example, in U.S. Pub. No. 2008/0021545, the disclosure of which is incorporated herein in its entirety by reference.

As previously noted, the composition may incorporate one or more therapeutic agents which are carried by the composition to the wound site. Alternatively, the composition may carry reagents which react to form a therapeutic agent in situ. In one embodiment, the composition delivers nanofibers containing tumor shrinking substances to the site of a tumor.

The ability to handle the composition in the form of a blob of nanofibers laparoscopically, while preserving the ability to remove the blob with forceps, as a surgical sponge is removed, is another use for the compositions described herein.

Forming the Nanofiber-Reinforced Composition

Nanofibers and microfibers for the biocompatible composition 20 may be fabricated according to a variety of methods known in the art including electrospinning, forming nanofibers by gas jet (NGJ), wet spinning, dry spinning, melt spinning, and gel spinning. Some of these methods start with a solution of a nanofiber-forming polymer dispersed in a suitable solvent. In the electrospinning method, for example, an electrical potential is applied between a droplet of the solution and a collector positioned below it. The droplet extends rapidly under the applied potential. The solvent evaporates from the solution, forming nanofibers before they reach the collector.

Suitable solvents for the nanofiber-forming polymer include organic liquids, such as acetone. For example, polycaprolactone (which may be formed by the catalytic polymerization of $\epsilon$-caprolactone) is dispersed in acetone solvent at a suitable temperature, such as 50° C.

Microfibers, e.g., with diameter from 5 to 50 μm and length from 1 mm to 500 mm, may be dispersed in the carrier liquid, before, during, or after incorporation of the electrospun or otherwise formed nanofibers.

Figure 2:
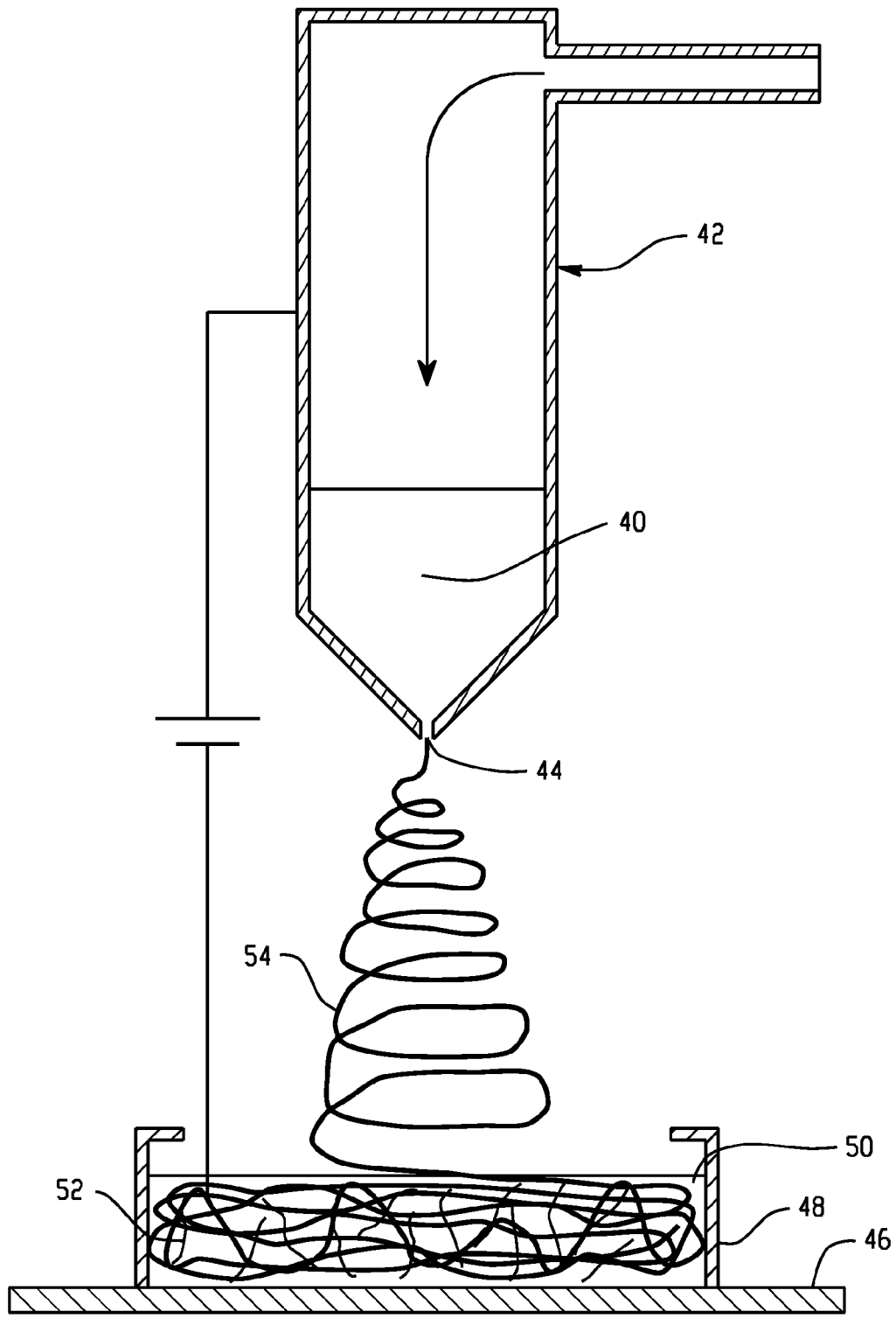
FIG. 2 illustrates an apparatus for forming a nanofiber-reinforced composition.
Figure 3:
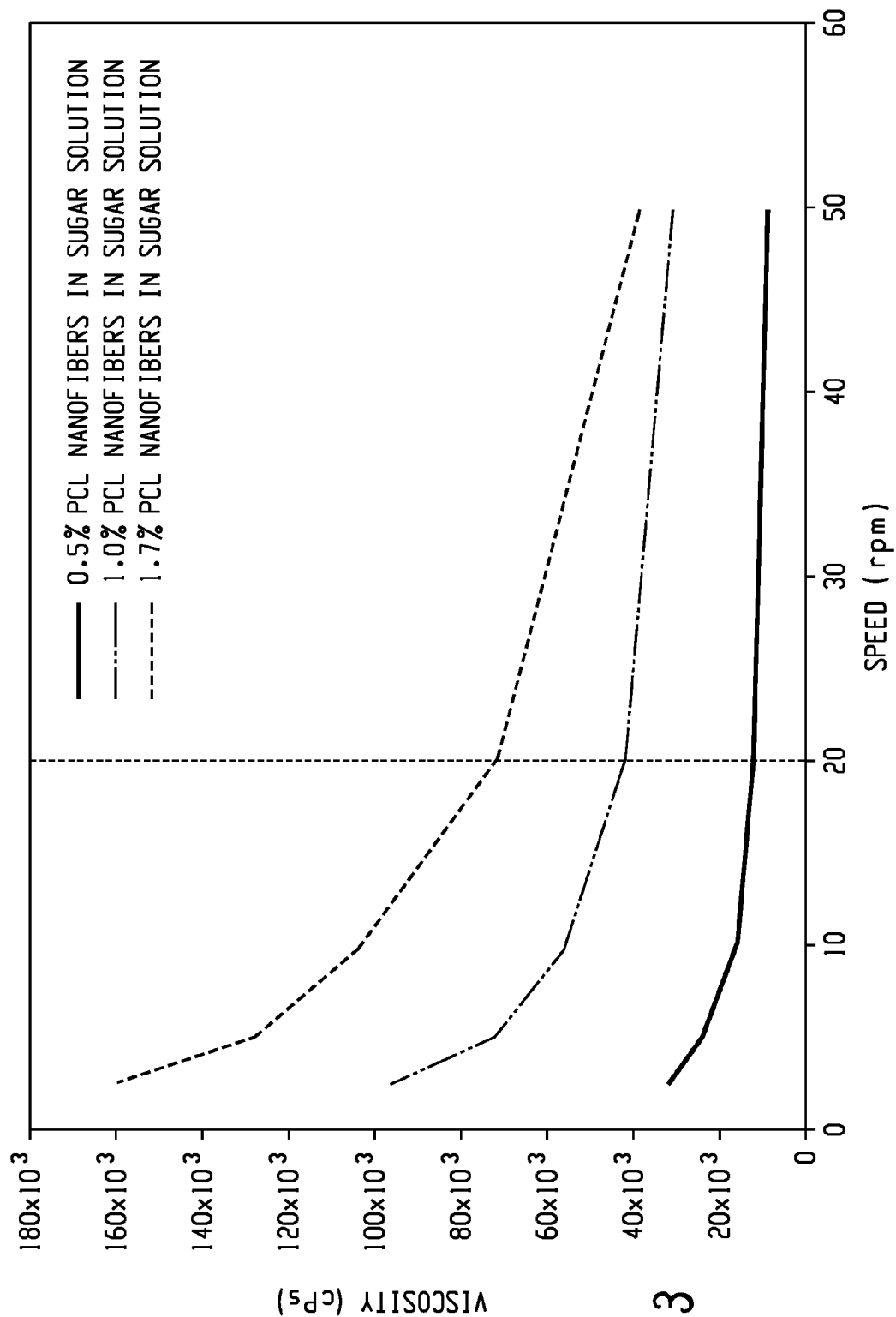
FIG. 3 is a graph of viscosity (cPs) vs. rotation speed for exemplary nanofiber-reinforced compositions.

An exemplary electrospinning apparatus is illustrated in FIG. 2. A polymer solution 40 is fed to a cone 42 with a small hole 44, which allows the polymer solution to pass through. A potential difference is applied between the cone 42 and a collector plate 46 by a high voltage supply.

A container 48 of sugar solution 50 is provided. Sugar is used here to refer to sugar molecules, oligomers, polymers, and combinations thereof. The sugar solution may be formed, for example, by dissolving dextran in water at an elevated temperature, such as about 100° C., and cooling the solution. The solution may be sterilized. Optionally, microfibers 52 are added to the formed sugar solution. The container holding the sugar solution 50 and optional microfibers 52 is positioned to receive the electrospun nanofibers 54, as they are formed. The electrospun nanofibers fall onto the surface of the sugar solution, which may be stirred gently to aid incorporation of the nanofibers and dispersion. The electrospinning may be performed in a laminar flow hood to ensure that sterility is maintained. Electrospinning is continued until a desired concentration of nanofibers 54 in the solution is achieved.

During electrospinning, the nanofibers may be completely dry when they land on top of each other, and therefore able to slide freely over each other or even to move apart. In one embodiment, the electrospun or otherwise formed nanofibers are collected together before they have solidified. The nanofibers then stick together at crossing points, that is, conglutinate. The degree of conglutination can be controlled during collection of the nanofibers. The layers of fibers thus formed tend to stay where they are put, and thereby improve anti-adhesion performance of the composition when applied to an organ.

Electrospinning is particularly suitable for fabricating the exemplary nanofibers inasmuch as it tends to produce very thin (i.e. fine denier) fibers. Typically electrospun nanofibers fibers can be produced having very small diameters, usually on the order of about 3 nanometers to about 3000 nanometers. In one embodiment, the electrospun nanofibers have a diameter of about 10 nanometers to about 500 nanometers, and in one specific embodiment, from about 10 nanometers to about 100 nanometers.

Buckling coils of nanofibers are created when a wet jet, such as is used in the electrospinning process, impinges on a solid or liquid surface. The diameter of the coil depends on diameter of the jet. Diameters of the coils may range from 1 micron to 100 micron, with diameters of 5 to 50 microns being particularly suitable.

Another method for producing nanofibers is known as the nanofibers by gas jet (NGJ) method. In this method, a device having an inner tube and a coaxial outer tube with a sidearm is provided. The inner tube is recessed from the edge of the outer tube, thus creating a thin film-forming region. Polymer melt is fed in through the sidearm and fills the empty space between the inner tube and the outer tube. The polymer melt continues to flow toward the effluent end of the inner tube until it contacts the effluent gas jet at the edge of the inner tube where it opens into the outer tube. The gas jet impinging on the melt creates a thin film of polymer melt in the region between the edges of the inner and outer tubes, which travels to the effluent end of the outer tube where it is ejected forming a turbulent cloud of nanofibers.

Other methods for forming nanofibers, which may be used herein are disclosed, for example, in U.S. Pat. Nos. 6,382,526 and 6,520,425, and U.S. Pub. No. 2007/0207179, the disclosures of which are incorporated herein by reference. Therapeutic agents may be dispersed in the carrier liquid or dispersed in the polymer solution or otherwise incorporated in to the composition.

Without intending to limit the scope of the exemplary embodiment, the following examples demonstrate properties of the reinforced composition

EXAMPLES

A solution comprising 20 wt. % of polycaprolactone in acetone was formed by dissolving polycaprolactone with a $M_w$ of 65,000 in acetone at 50° C. The solution was filtered through a sterile filter that had 0.45 micrometer holes to ensure that the solution was free of unwanted organisms. A sugar solution comprising 30% by weight of dextran ($M_w$ 100,000-200,000 g/mol) was formed by dissolving dextran in water at a temperature of 100° C. The solution was sterilized in an autoclave. The polycaprolactone solution was transferred to a sterile glass pipette and connected, via a metal wire, to a high voltage power supply, as illustrated in FIG. 2.

Nanofiber-reinforced compositions A, B, and C were formed by electrospinning poly(caprolactone) nanofibers from the pipette directly into the dextran solution (30 wt. % dextran). Electrospinning was performed in a laminar flow hood to ensure sterility. The nanofibers landing on the surface of the dextran solution were incorporated by gently stirring the mixture until it was homogeneous. In the resulting compositions A, B, and C, the nanofiber concentrations were 0.5%, 1%, and 1.7%, by weight, respectively.

The twisting of the nanofibers into yarn like structures could be readily observed as composition B was spread on the hands by gentle rubbing motion. The yarn-like structures were even more evident as the composition is washed off. The rubbing of one hand over the other is similar to the motion of organs sliding past each other and thus demonstrates the effectiveness of the composition.

The addition of 6 mm diameter platelets, made with a paper punch, from polyester films used to protect sheets of paper in a ring binder, effectively reduced the formation of yarn-like structures during the hand-washing of composition B. Addition of such platelets stabilized the useful properties of the composition. The nanofibers and platelets thus had a synergistic action. The nanofibers held the platelets in place and the platelets kept the fiber from twisting into yarn like segments. Smaller diameter platelets may also work well, such as platelets from 0.1 mm to 10 mm wide.

Viscosity:

The viscosity of compositions A, B, and C was measured using a Brookfield HB, spindle number 6 at 25° C., as described above. Table 1 shows the viscosities obtained. These results are shown graphically in FIG. 3. Composition B has a viscosity which is particularly suited to the exemplary application as a barrier for a surgical wound.

TABLE 1

| Speed | Viscosity (cPs) | | |
|---|---|---|---|
| (rpm) | A (0.50% PCL) | B (1.00% PCL) | C (1.70% PCL) |
| 2.5 | 32000 | 96000 | 160000 |
| 5 | 24000 | 72000 | 128000 |
| 10 | 16000 | 56000 | 104000 |
| 20 | 12000 | 42000 | 72000 |
| 50 | 8800 | 32000 | 40000 |

Figure 4:
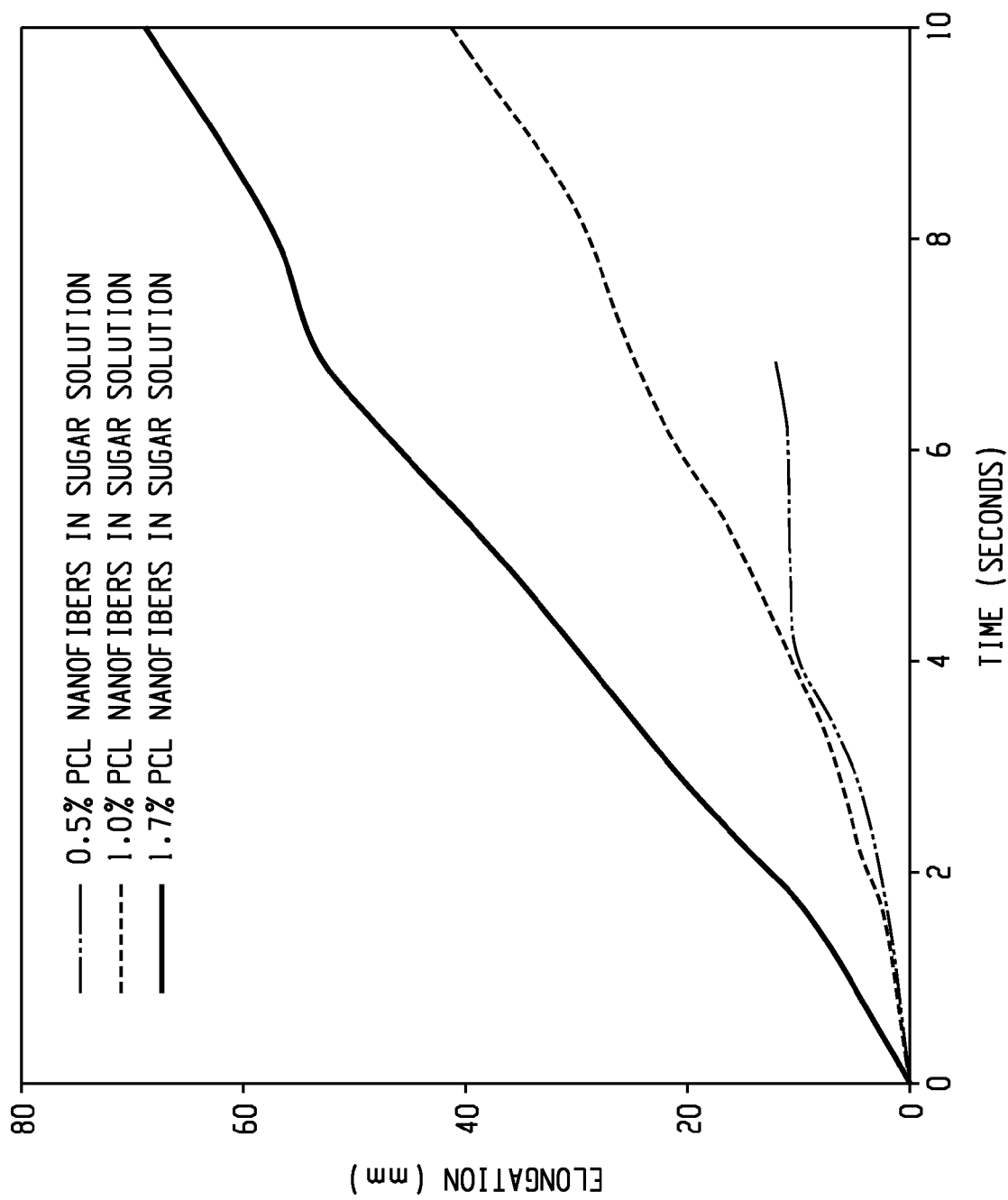
FIG. 4 is a plot of elongation vs. time for the exemplary nanofiber-reinforced compositions.

Elongation:

An elongation test was performed by filling two small tubes having an internal diameter of 4 mm with the composition A, B, or C. The tubes were temporarily joined end to end and kept in contact with each other while they were filled with the composition. The two tubes were then separated until a liquid column formed between the two previously joined ends of the tubes broke. The lengths of liquid columns just before they broke were recorded. The results of elongation vs. time are shown in FIG. 4. Material B elongated to 41 mm before break, which is a suitable elongation for a barrier material. Material A elongated to only 12 mm, and material C elongated to 69 mm.

Smear Test

A measured quantity of the composition A, B, or C was placed on a sheet of black polyethylene. A strip of cloth was placed on top of the material, and a 225 gram metal bar was placed on top of the cloth. The strip of fabric was pulled by hand at a rate of around 5 mm per second. The material was spread primarily in the direction of pulling. The length of the smeared material on the polyethylene sheet was measured. Two quantities of material, 0.2 and 0.4 ml, were tested for each of the compositions A, B, and C. The length of the smear was about the same for each of the quantities of the material in the test, indicating that the amount of material tested had only a minor effect on the smear length. The smear test indicates the ease with which a suitable barrier layer can be created by spreading the composition on the surface.

Application to a Wound Site

Composition B was applied to a pig's ovary which had been injured to simulate a laparoscopic surgery wound. The composition spread easily and remained on the wound site.

The exemplary embodiment has been described with reference to the preferred embodiment. Obviously, modifications and alterations will occur to others upon reading and understanding the preceding detailed description. It is intended that the exemplary embodiment be construed as including all such modifications and alterations insofar as they come within the scope of the appended claims or the equivalents thereof.

The invention claimed is:

1. A nanofiber-reinforced composition comprising:
   a carrier liquid including a soluble sugar;
   nanofibers dispersed in the carrier liquid; and
   platelets with a mean diameter of about 0.1 mm to about 10 mm dispersed in the carrier liquid.

2. The nanofiber-reinforced composition of claim 1, wherein the nanofibers are present in the nanofiber-reinforced composition at a concentration of at least 0.1 percent by weight.

3. The nanofiber-reinforced composition of claim 2, wherein the nanofibers are present in the nanofiber-reinforced composition at a concentration of at least 0.5 percent by weight.

4. The nanofiber-reinforced composition of claim 1, wherein the nanofibers are present in the nanofiber-reinforced composition at a concentration of up to 5 percent by weight.

5. The nanofiber-reinforced composition of claim 1, wherein the nanofibers have a diameter of less than 3000 nanometers.

6. The nanofiber-reinforced composition of claim 1, wherein the nanofibers comprise polycaprolactone.

7. The nanofiber-reinforced composition of claim 1, further comprising microfibers dispersed in the carrier liquid.

8. The nanofiber-reinforced composition of claim 7, wherein the microfibers have a diameter of at least 5 micrometers.

9. The nanofiber-reinforced composition of claim 7, wherein the microfibers are present in the nanofiber-reinforced composition at a concentration of 0.1 to 5 percent by weight.

10. The nanofiber-reinforced composition of claim 7, wherein the nanofibers and microfibers are present in the nanofiber-reinforced composition at a total concentration of less than 5 percent by weight.

11. The nanofiber-reinforced composition of claim 1, wherein the soluble sugar comprises dextran.

12. The nanofiber-reinforced composition of claim 1, wherein the soluble sugar is present in the carrier liquid at a concentration of at least 20 weight percent.

13. The nanofiber-reinforced composition of claim 1, wherein the soluble sugar has a weight average molecular weight of at least 50,000.

14. The nanofiber-reinforced composition of claim 1, further comprising at least one of flakes, dissolved substances, particles, colloids, and micelles, and therapeutic agents.

15. The nanofiber-reinforced composition of claim 1, wherein the nanofiber-reinforced composition has a viscosity of from 10,000 to 80,000 cPs when measured at a temperature of 25° C. and a rotation speed of 20 revolutions per minute such that the nanofiber-reinforced composition can pass through a tube having a diameter of less than 1 cm and can adhere to a wound site.

16. The nanofiber-reinforced composition of claim 1, wherein the platelets have a thickness of less than half the diameter.

17. The nanofiber-reinforced composition of claim 1, wherein the platelets are formed from a biodegradable polymer selected from the group consisting of poly(caprolactone), poly(L-lactic acid), poly(glycolic acid), poly(lactic-co-glycolic acid), poly($\beta$-hydroxybuyrate), poly(acrylic acid), poly(hydroxylethylmethacrylate), cellulose, cellulose derivatives, protein, polyanhydrides, and combinations thereof.

18. The nanofiber-reinforced composition of claim 1, wherein the platelets are formed from a polyester.

19. An applicator comprising:
   a container which holds an amount of a nanofiber-reinforced composition comprising:
      a carrier liquid including a soluble sugar;
      nanofibers dispersed in the carrier liquid; and
      platelets with a mean diameter of about 0.1 mm to about 10 mm dispersed in the carrier liquid;
   a tube, fluidly connected with the container, for introducing the nanofiber-reinforced composition into a body of a subject.

20. The applicator of claim 19, wherein the nanofiber-reinforced composition is devoid of a mesh support.

21. The applicator of claim 19, wherein the nanofiber-reinforced composition has a viscosity which allows it to pass through a tube having a diameter of less than 1 cm, which viscosity being sufficient to allow the composition to adhere to a wound site.

22. The applicator of claim 21, wherein the nanofiber-reinforced composition has a viscosity of from 10,000 to 80,000 cPs when measured at a temperature of 25° C. and a rotation speed of 20 revolutions per minute.

23. A method comprising:
   introducing a nanofiber-reinforced composition into a body of a subject where the nanofiber-reinforced composition comprises:
      a carrier liquid including a soluble sugar;
      nanofibers dispersed in the carrier liquid; and platelets with a mean diameter of about 0.1 mm to about 10 mm dispersed in the carrier liquid.

24. The method of claim 23, wherein the introducing includes introducing the nanofiber-reinforced composition into a subject's body though a tube.

25. The method of claim 24, wherein the tube comprises an outlet defined by at least one pair of surfaces and the method comprises moving the surfaces relative to one another as the nanofiber-reinforced composition is released into the body from the outlet.

26. The method of claim 24, further comprising positioning the tube adjacent a wound site within the subject's body and introducing the composition through the tube to the wound site.

27. A method of forming the composition of claim 1, comprising:
  forming nanofibers;
  combining the nanofibers with the carrier liquid including a soluble sugar; and dispersing the platelets with a mean diameter of about 0.1 mm to about 10 mm in the carrier liquid.

28. The method of claim 27, wherein the combining includes electrospinning the nanofibers directly into the carrier liquid.

29. The method of claim 27, further comprising combining at least one of microfibers, flakes, dissolved substances, particles, colloids, micelles, and therapeutic agents with the carrier liquid.

30. A method of providing an adhesive barrier at a wound site comprising:
  introducing a nanofiber-reinforced composition to a subject's body through a tube having an outlet positioned adjacent the wound site, the nanofiber-reinforced composition having a viscosity which causes it to adhere to the wound site or neighboring tissue to form an adhesive barrier thereon;
wherein the nanofiber-reinforced composition comprises:
  a carrier liquid including a soluble sugar;
  nanofibers dispersed in the carrier liquid; and
  platelets with a mean diameter of about 0.1 mm to about 10 mm dispersed in the carrier liquid.

* * * * *